United States Patent
Ramakrishnan et al.

(10) Patent No.: US 8,401,660 B2
(45) Date of Patent: Mar. 19, 2013

(54) POLLING MECHANISM IN A MEDICAL IMPLANT BASED SYSTEM

(75) Inventors: Sthanunathan Ramakrishnan, Bangalore (IN); Divyesh Kumar Shah, Bangalore (IN)

(73) Assignee: Texas Instruments Incorporated, Dallas, TX (US)

( * ) Notice: Subject to any disclaimer, the term of this patent is extended or adjusted under 35 U.S.C. 154(b) by 670 days.

(21) Appl. No.: 12/536,579

(22) Filed: Aug. 6, 2009

(65) Prior Publication Data

US 2010/0036461 A1    Feb. 11, 2010

Related U.S. Application Data

(60) Provisional application No. 61/086,663, filed on Aug. 6, 2008.

(51) Int. Cl.
*A61N 1/08* (2006.01)

(52) U.S. Cl. .......................... 607/60; 607/59

(58) Field of Classification Search .................. 607/32, 607/60
See application file for complete search history.

(56) References Cited

U.S. PATENT DOCUMENTS

| 2005/0240245 A1* | 10/2005 | Bange et al. ............. 607/60 |
| 2010/0023085 A1* | 1/2010 | Wu et al. ............ 607/30 |

* cited by examiner

*Primary Examiner* — Carl H Layno
*Assistant Examiner* — Paula J Stice
(74) *Attorney, Agent, or Firm* — Michael A. Davis, Jr.; W. James Brady; Frederick J. Telecky, Jr.

(57) ABSTRACT

Polling mechanism in a medical implant based system. A method for operating a receiver includes searching for a signal by a receiver. The method further includes entering into an inactive state for a predefined time interval, if the signal is not detected. The method also includes altering at least one of sensitivity and the predefined time interval if number of times the searching is performed without detecting the signal exceeds a threshold. Moreover, the method includes searching for the signal with at least one of altered sensitivity and altered predefined time when the receiver enters into an active state.

5 Claims, 3 Drawing Sheets

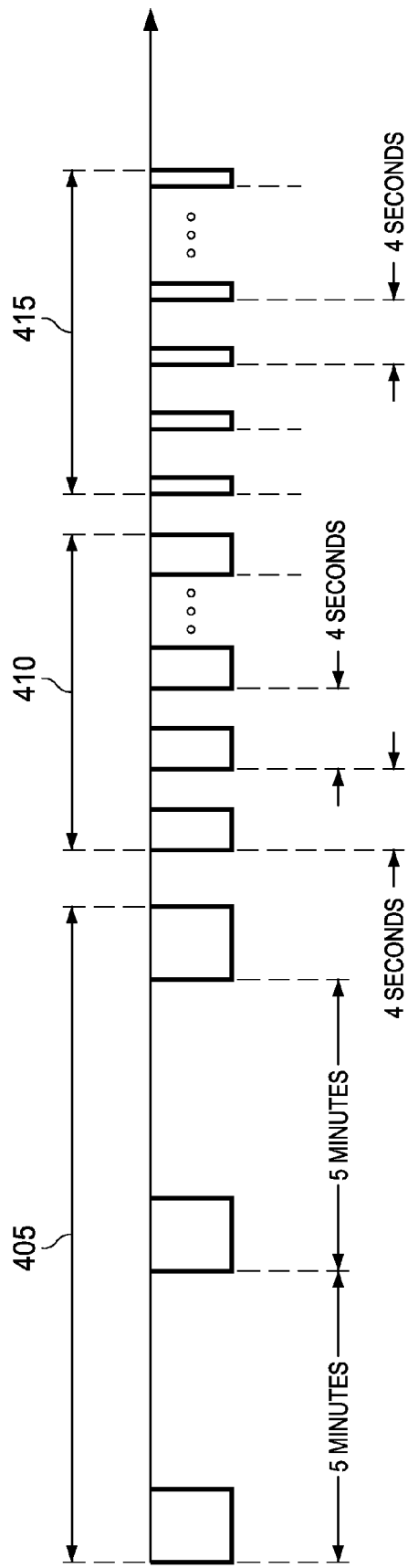
FIG. 4
FIG. 5
FIG. 6

POLLING MECHANISM IN A MEDICAL IMPLANT BASED SYSTEM

REFERENCE TO PRIORITY APPLICATION

This application claims priority from U.S. Provisional Application Ser. No. 61/086,663 filed Aug. 6, 2008, entitled "Wake-up signaling in MICS implants", U.S. Non-provisional application Ser. No. 12/536,520 filed Aug. 6, 2009, entitled "Signaling in a medical implant based system", and U.S. Non-provisional application Ser. No. 12/536,562 filed Aug. 6, 2009, entitled "Parallel search circuit for a medical implant receiver", which are incorporated herein by reference in their entirety.

TECHNICAL FIELD

Embodiments of the disclosure relate to polling mechanism in a medical implant based system.

BACKGROUND

A medical implant based system includes a medical controller and a medical implant. The medical implant is present inside body of a living organism and the medical controller is external. Power consumption of the medical implant is one of the major determinants of lifetime of the medical implant. The power consumption in a medical implant transceiver forms a significant portion of the overall power consumption in the medical implant. Hence, it is desired to maximize efficiency of the medical implant transceiver to increase lifetime of the medical implant.

The power of the medical implant transceiver is utilized for performing various functions. In one example, the power consumption in the medical implant transceiver is dominated by a listen mode of the medical implant transceiver. In the listen mode, the medical implant transceiver wakes up periodically, every few seconds, and searches for a signal for association. In an associated state also, the medical implant transceiver follows a procedure similar to the listen mode, and wakes up periodically, every few seconds, and searches for the signal for association. In one example, the medical implant transceiver in associated state follows the procedure because the medical implant transceiver needs to detect another medical controller transceiver. For example, if the medical implant transceiver is initially associated with the medical controller transceiver at home, but the living organism including the medical implant transceiver travels to a Doctor's office, then the medical implant transceiver needs to detect and associate with the medical controller transceiver at the Doctor's office. Hence the medical implant transceiver wakes up with the periodicity even when the medical implant transceiver is associated, to detect other medical controller transceivers. However, waking up in the associated state with a periodicity similar to that in the listen mode leads to power wastage when the medical implant transceiver has to search for the signal with low strength as the time for which the medical implant transceiver has to listen to the channel increases for signals with low strength.

SUMMARY

An example of a method for operating a receiver includes searching for a signal. The method further includes entering into an inactive state for a predefined time interval, if the signal is not detected. The method also includes altering at least one of sensitivity and the predefined time interval if number of times the searching is performed without detecting the signal exceeds a threshold. Moreover, the method includes searching for the signal with at least one of altered sensitivity and altered predefined time when the first receiver enters into an active state.

An example of a method for operating a receiver in a medical implant based system includes receiving a signal. The method further includes checking for presence of information indicative of a polling schedule in the signal. The method also includes entering into an inactive state for a time interval indicated in the polling schedule, if the information indicative of the polling schedule is detected in the signal. Moreover, the method includes awakening at end of the time interval.

An example of a system includes a medical implant transceiver. The medical implant receiver includes a radio frequency receiver that searches for a signal. The medical implant receiver also includes a processing circuit responsive to search to cause the medical implant receiver to enter into an inactive state for a predefined time interval if the signal is not detected, to alter at least one of sensitivity and the predefined time interval if number of times the searching is performed without detecting the signal exceeds a threshold, and to cause the radio frequency receiver to search for the signal with at least one of altered sensitivity and altered predefined time when the medical implant receiver enters into an active state.

BRIEF DESCRIPTION OF THE VIEWS OF DRAWINGS

In the accompanying figures, similar reference numerals may refer to identical or functionally similar elements. These reference numerals are used in the detailed description to illustrate various embodiments and to explain various aspects and advantages of the disclosure.

FIG. 4 is an exemplary illustration of an optimized polling schedule, in accordance with one embodiment;

FIG. 5 illustrates a portion of medical implant transceiver, in accordance with one embodiment; and FIG. 6 illustrates a portion of a medical controller transceiver, in accordance with one embodiment.

DETAILED DESCRIPTION OF THE EMBODIMENTS

Figure 1:
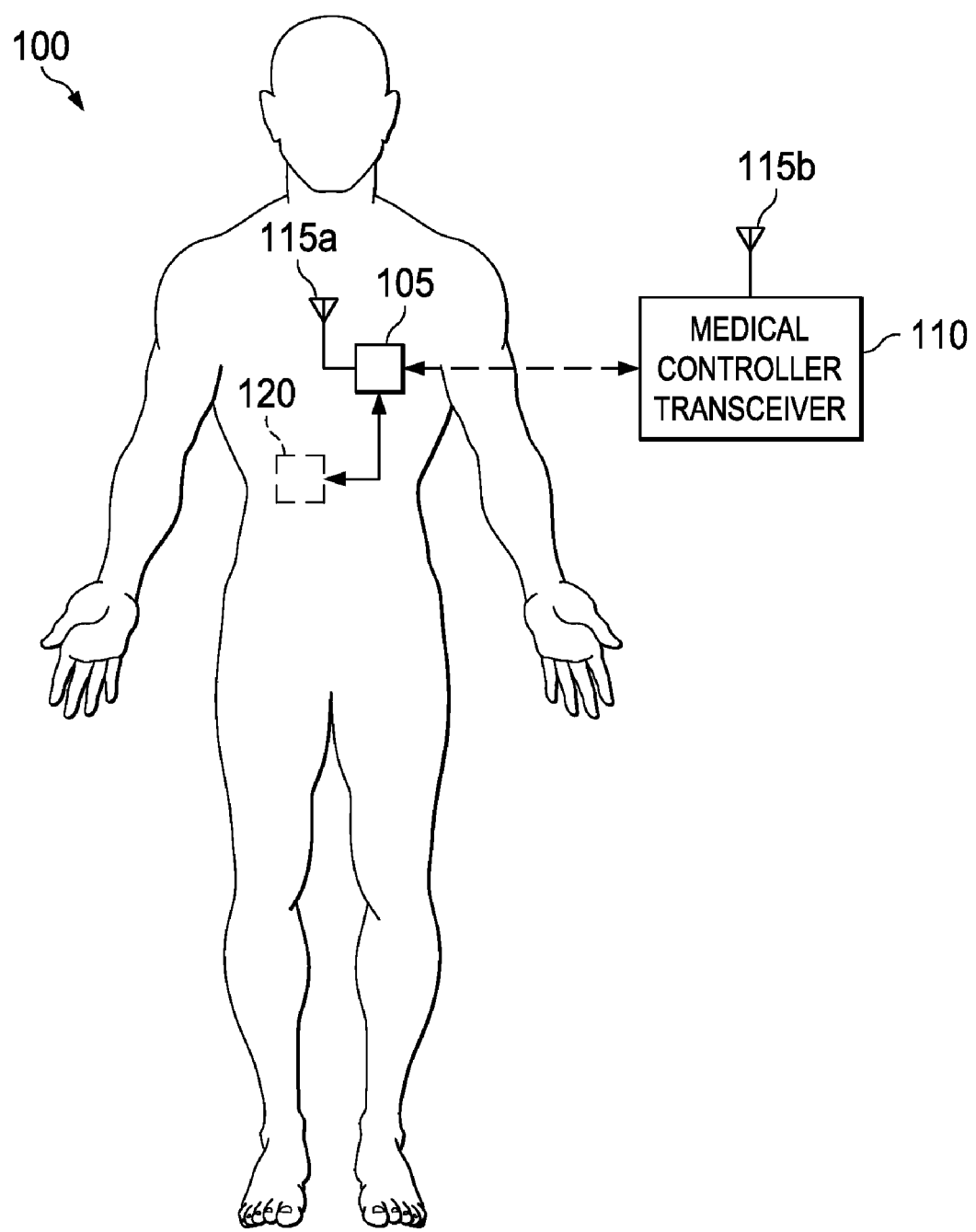
FIG. 1 illustrates an environment, in accordance with one embodiment.

FIG. 1 illustrates an environment 100 including, for example a medical implant based system. Examples of the environment 100 include, but are not limited to, intensive care units (ICUs), hospital wards, and home environment. The environment 100 includes a receiver, for example a medical implant receiver 105, herein referred to as the implant receiver 105, and a medical controller transceiver 110, herein referred to as the controller transceiver 110.

The implant receiver 105 includes or is connected to an antenna 115a to receive signals. The implant receiver 105 can also include or be connected to sensors, for example a sensor 120. Each sensor monitors and senses various health details. Examples of the sensors include, but are not limited to, pacemakers and brain sensors. The controller transceiver 110 also includes or is connected to an antenna 115b to transmit and receive signals.

The implant receiver 105 and the controller transceiver 110 can communicate with each other in a medical implant communication service (MICS) frequency band. The MICS frequency band ranges from 402 megahertz (MHz) to 405 MHz. The implant receiver 105 and the controller transceiver 110 can also communicate with each other in a medical data services (MEDS) frequency band. The MEDS frequency band ranges from 401 MHz to 402 MHz, and from 405 MHz to 406 MHz.

A communication session is initiated by the controller transceiver 110. The controller transceiver 110 selects a channel for transmission based on certain parameters. In one example, the controller transceiver 110 selects either a least interfered channel or a channel which has interference power below a threshold. The selection process can be referred to as "Listen Before Talk" (LBT). The controller transceiver 110 then transmits a signal in the channel.

The implant receiver 105 can have two states, an associated state and an unassociated state. The associated state can be defined as a state in which the implant receiver 105 is associated with the controller transceiver 110. The unassociated state can be defined as a state in which the implant receiver 105 is not associated with the controller transceiver 110. The implant receiver 105 transitions between an active state (awakened state) and an inactive state (a sleep state) irrespective of being in the associated state or the unassociated state. The implant receiver 105 searches for a signal for association in the unassociated state and for a poll signal or the signal for association in the associated state.

In one example, the implant receiver 105 wakes up with the same periodicity, every few seconds, in both the unassociated state and the associated state for detecting and associating with medical controller transceivers. However, this leads to power wastage. It is desired to have different periodicity for the unassociated state and the associated state to save power.

The periodicity or the time duration for the inactive state is based on operating conditions and it is desired to have the implant receiver 105 enter into the inactive state and the active state based on the operating conditions to optimize power consumption. Further, strength of the signal might also differ based on the operating conditions and it is desired to have the implant receiver 105 search for signals at different sensitivity based on the operating conditions to optimize power consumption.

In one example, the implant receiver 105 is associated with the controller transceiver 110 at home. The living organism including the implant receiver 105 travels from the home to a doctor's office. It might take around 15 minutes to get close to another controller transceiver at Doctor's office from the controller transceiver 110 at the home. In illustrated example, when the implant receiver 105 is associated with the controller transceiver 110 at home then the time duration between two poll signals can be 5 minutes. The controller transceiver 110 at the home can transmit the signal once every 5 minutes, to synchronize with the implant receiver 105 and also to indicate to the implant receiver 105 that the implant receiver 105 is in the vicinity of the controller transceiver 110 with which the implant receiver 105 is associated. The power consumption is reduced as the implant receiver 105 has to wake up once every 5 minutes instead of once every few seconds. If the implant receiver 105 does not detect the signal from the controller transceiver 110 for 3 consecutive attempts, the implant receiver 105 may decide that the implant receiver 105 is not in close proximity to the controller transceiver 110 and de-associate with the controller transceiver 110. The implant receiver 105 then wakes up periodically with a period of the order of few seconds to detect a controller transceiver. The implant receiver 105 might be associated with the controller transceiver 110 at the home for around 8-12 hours a day and hence having different periodicity in the associated case as compared to that in the unassociated case saves power and current.

In another example, the operating condition can include a hospital environment. Low sensitivity and low latency is desired at the hospital because the living organism including the implant receiver 105 is in close proximity to the controller transceiver 110. The latency for initiating connection with the controller transceiver 110 at the hospital needs to be low as the doctor may not desire to wait for long for the implant receiver 105 to associate with the controller transceiver 110.

In yet another example, the operating condition can include a home environment. High sensitivity is desired at the home because the living organism including the implant receiver 105 needs to have freedom to move around and might not be in close proximity to the controller transceiver 110. The data that needs to be transferred is less and sporadic, and hence the latency can be high.

In still another example, the operating condition may change dynamically when the living organism is travelling. It is desired that the implant receiver 105 is adaptable to dynamically varying conditions.

Various programmable sensitivity modes and time schedules for entering into the inactive state can be included in the implant receiver 105 to adapt to different operating conditions. A sensitivity mode and a time schedule can together be referred to as a polling schedule. In the unassociated state, the duration of the inactive state and the sensitivity can be determined unilaterally by the implant receiver 105 and can be predefined while in the associated state, the duration and the sensitivity can be communicated to the implant receiver 105 by the controller transceiver 110. A method to optimize power consumption of the implant receiver 105 under different operating conditions is explained in conjunction with FIG. 2.

Figure 2:
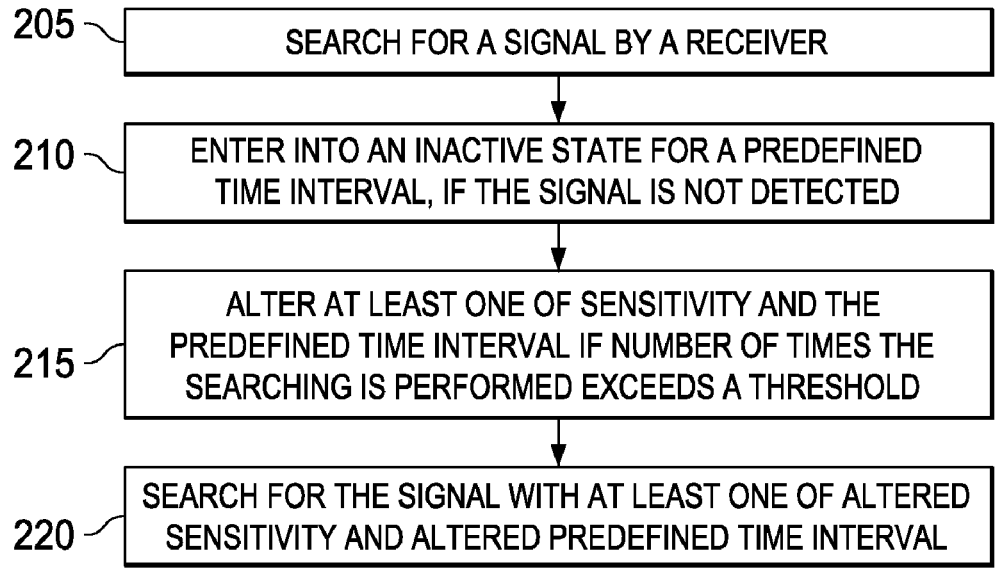
FIG. 2 illustrates a method for operating a receiver, in accordance with one embodiment.

Referring to FIG. 2, at step 205, a search for a signal is performed by a receiver, for example a medical implant receiver, hereinafter referred to as the implant receiver.

In one aspect, the implant receiver is in an unassociated state and searches for a signal for association based on a predefined polling schedule. The predefined polling schedule includes a sensitivity mode and a predefined time interval.

In another aspect, the implant receiver is in an associated state and searches for the signal for association or a poll signal based on another predefined polling schedule. The predefined polling schedule is different for the implant receiver when the implant receiver is in the unassociated state and when the implant receiver is in the associated state.

At step 210, the implant receiver enters into an inactive state for the predefined time interval, if the signal is not detected.

In some embodiments, if the poll signal is detected then the implant receiver detects that the implant receiver is associated and continues to follow the predefined polling schedule of the associated state.

In some embodiments, step 205 and step 210 are repeated for a predefined number of times.

At step 215, at least one of sensitivity and the predefined time interval is altered if number of times the search is performed without detecting the signal exceeds a threshold. The implant receiver searches for the signal until it detects the signal.

In one example, the signal might not be detected as the sensitivity mode of the implant receiver might not be sufficient to detect the signal. The implant receiver can then alter the sensitivity to detect the signal. In some embodiments, the implant receiver can also alter the predefined time interval to detect the signal. Several polling schedules, for example a first polling schedule and a second polling schedule, can be embedded into the implant receiver. Each polling schedule includes a sensitivity mode and a time interval. The first polling schedule includes a first sensitivity mode and a first time interval. The second polling schedule includes a second sensitivity mode and a second time interval. Two polling schedule can be referred to as being different from each other when at least one of the sensitivity mode and the time interval differs between the two. The implant receiver can switch between the polling schedules periodically or based on certain thresholds or upon direction from the controller transceiver with which the implant receiver is associated. The switching can be referred to as altering the sensitivity mode and the predefined time interval. The implant receiver also switches between the polling schedules based on whether the implant receiver is in the associated state or the unassociated state. For example, when a living organism including the implant receiver in unassociated state reaches home then the implant receiver searches for the signal in low sensitivity and low latency mode. It might happen that the signal is not detected in three consecutive cycles of entering into the active state by the implant receiver. The implant receiver then checks the threshold. If the threshold is two then the implant receiver activates a high sensitivity and high latency mode. In one embodiment, the switching of polling schedules can include switching from a first circuit capable of operating the receiver at the first polling schedule to a second circuit capable of operating the receiver at the second polling schedule. The circuits can be present in the implant receiver. For example, if the switching needs to be performed from high sensitivity mode to low sensitivity mode then a circuit that detects signal using correlators, accumulators, mixers, and peak to off-peak estimators can be inactivated, and a circuit that detects signal using power estimation technique can be activated.

At step 220, the implant receiver searches for the signal with at least one of altered sensitivity and altered predefined time interval. The implant receiver enters into the inactive state and the active state based on altered time interval.

Figure 3:
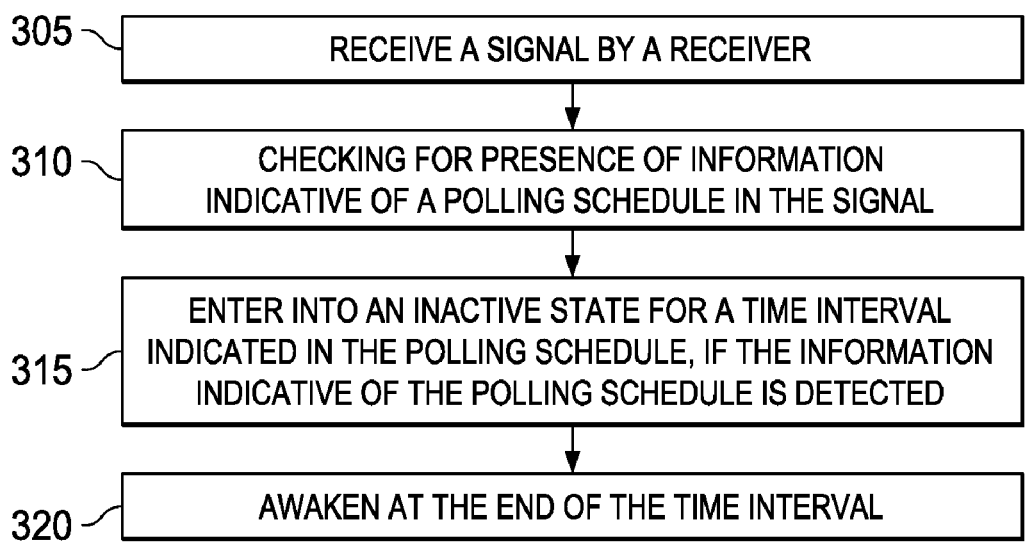
FIG. 3 illustrates a method for operating of a receiver, in accordance with another embodiment.

Referring to FIG. 3 now, at step 305, a signal is received by a receiver, for example a medical implant receiver, hereinafter referred to as the implant receiver. The signal can be a signal for association or a poll signal or any other signal. The implant receiver after processing the signal associates with a medical controller transceiver, hereinafter referred to as the controller transceiver, which sent the signal.

At step 310, checks for presence of information indicative of a polling schedule in the signal.

The controller transceiver determines the polling schedule based on operating conditions of the implant receiver and the controller transceiver. Several polling schedules can be embedded into the controller transceiver. The controller transceiver can determine the polling schedule in response to an input from a user of a controller or the user can specify the polling schedule. The controller transceiver then sends information indicative of the polling schedule to the implant receiver. The information indicative of the polling schedule or the polling schedule can then be sent in the signal, for example in the signal for association or the poll signal or any other signal.

At step 315, the implant receiver enters into an inactive state for a time interval indicated in the polling schedule, if the information indicative of the polling schedule is detected.

In some embodiments, the information indicative of the polling schedule might not be present, and the controller transceiver can then send the signal based on a predefined polling schedule and the implant receiver can search and detect the signal based on the predefined polling schedule. The predefined polling schedule can be present with the controller transceiver and the implant receiver a priori.

At step 320, the implant receiver awakens at the end of the time interval. The implant receiver then searches for the signal. The awakening includes entering into the active state.

In one embodiment, it might happen that the implant receiver does not find any signal after awakening. The implant receiver can then again enter into the inactive state for the time interval. This might happen in the case when the implant receiver is associated with the controller transceiver at the hospital but the living organism having the implant receiver has moved out of the hospital. The implant receiver sleeps and wakes up to search for the signal but does not find the signal to be tracked. The number of times the implant receiver sleeps and wakes up is checked against a threshold. If the number exceeds the threshold then the implant receiver can activate the predefined schedule and de-associate with the controller transceiver at the hospital.

In another embodiment, the implant receiver also detects sensitivity from the polling schedule and searches for a subsequent signal based on the sensitivity. The implant receiver might find the subsequent signal and decide that the implant receiver is associated. The subsequent signal is transmitted by the controller transceiver based on the polling schedule sent to the implant receiver by the controller transceiver.

FIG. 4 is an exemplary illustration of an optimized polling schedule. The optimized polling schedule can be based on the operating conditions, for example desired latency and desired sensitivity, of the implant receiver. In the illustrated example, a portion 405 represents high latency, high sensitivity operating condition, when the implant receiver is in the home environment and associated with a controller transceiver. The implant receiver wakes up every 5 minutes and listens for the signal for a predefined duration of time. The duration of the portion 405 is 10 minutes. The implant receiver searches for the signal, for example, for three consecutive times. In illustrated example, the signal is not detected and hence the implant receiver switches to high sensitivity and low latency polls. A portion 410 corresponds to the high sensitivity and low latency polls. In the illustrated example, the signal is not detected in the portion 410 and hence the implant receiver switches to low latency and low sensitivity polls. The portion 410 can correspond to a time when the living organism including the implant receiver is travelling and not in proximity to the controller transceiver. A portion 415 represents the low latency and low sensitivity polls. The power is saved by using optimized schedule as the sensitivity can be varied to choose low sensitivity mode in which the time spent in active state is reduced. Further, the time interval for inactive state can be different for the associated and unassociated state which further helps in power saving in the associated mode.

Referring to FIG. 5, a portion of the implant transceiver, for example the implant receiver 105 includes a radio frequency receiver 505 that receives a band of channels through an antenna 115*a*. The implant receiver 105 includes a processing circuit 510 that is coupled to the radio frequency receiver 505. The radio frequency receiver 505 can be centered in middle of MICS+MEDS band to receive the band of channels. The processing circuit 510 performs the techniques of the implant receiver 105 described herein. In one example, the processing circuit 510 processes the signal to detect information indicative of a polling schedule in the signal. Further, the processing circuit 510 processes the signal to cause the implant receiver 105 to enter into an inactive state for a time interval indicated in the polling schedule. Furthermore, the processing circuit 510 processes the signal to cause the implant receiver 105 to enter into an active state at the end of the time interval.

In another example, the processing circuit 510 causes the implant receiver 105 to enter into an inactive state for a predefined time interval if the signal is not detected, alters at least one of sensitivity and the predefined time interval if number of times the searching is performed without detecting the signal exceeds a threshold, and causes the radio frequency receiver 505 to search for the signal with at least one of altered sensitivity and altered predefined time when the implant receiver 105 enters into an active state.

Referring to FIG. 6, a portion of the controller transceiver 110 includes a processing circuit 605 that is coupled to a radio frequency transmitter 610. The processing circuit 605 performs the techniques of the controller transceiver 110 described herein. In one example, the processing circuit 605 determines the polling schedule based on desired latency of polls. The radio frequency transmitter 610 transmits the signal having the polling schedule through an antenna 115*b*. A subsequent signal can then be transmitted based on the polling schedule.

In the foregoing discussion, the term "coupled" refers to either a direct electrical connection between the devices connected or an indirect connection through intermediary devices. The term "signal" means at least one current, voltage, charge, data, or other signal.

The foregoing description sets forth numerous specific details to convey a thorough understanding of embodiments of the disclosure. However, it will be apparent to one skilled in the art that embodiments of the disclosure may be practiced without these specific details. Some well-known features are not described in detail in order to avoid obscuring the disclosure. Other variations and embodiments are possible in light of above teachings, and it is thus intended that the scope of disclosure not be limited by this Detailed Description, but only by the Claims.

What is claimed is:

1. A method for operating a receiver in a medical implant system, the method comprising:
    in response to entering into an active state, searching for a signal for a duration of time;
    if the signal is not detected within the duration of time, entering into an inactive state for a time interval to reduce power consumption during the inactive state, and reentering into the active state in response to an end of the time interval;
    if the signal is detected within the duration of time, receiving the signal at the receiver, and checking for presence of information indicative of a polling schedule in the received signal;
    wherein the duration of time is: predefined if the information indicative of the polling schedule is not detected in the received signal; predefined if the information indicative of the polling schedule does not indicate the duration of time and otherwise altered as indicated in the polling schedule; and
    wherein the time interval is: predefined if the information indicative of the polling schedule is not detected in the received signal; predefined if the information indicative of the polling schedule does not indicate the time interval; and otherwise altered as indicated in the polling schedule.

2. The method as claimed in claim 1 and further comprising:
    determining the polling schedule by a medical controller transceiver;
    transmitting the signal to the receiver, wherein the signal includes information indicative of the polling schedule; and
    transmitting a subsequent signal based on the polling schedule.

3. The method as claimed in claim 1 and further comprising:
    searching for the signal until one of: reaching a threshold number of searches; and detecting the signal; and
    if the threshold number of searches is reached without detecting the signal, altering at least one of: the duration of time; and the time interval.

4. The method as claimed in claim 1 and further comprising:
    transmitting a subsequent signal based on the polling schedule.

5. The method as claimed in claim 1 and further comprising:
    searching for the signal until one of: reaching a threshold number of searches; and detecting the signal; and
    if the threshold number of searches is reached without detecting the signal, de-associating with a medical controller transceiver.

* * * * *